United States Patent
Li

(10) Patent No.: US 10,204,424 B2
(45) Date of Patent: Feb. 12, 2019

(54) COLOR IDENTIFYING SYSTEM, COLOR IDENTIFYING METHOD AND DISPLAY DEVICE

(71) Applicant: BOE Technology Group Co., Ltd., Beijing (CN)

(72) Inventor: Hui Li, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 155 days.

(21) Appl. No.: 15/307,551

(22) PCT Filed: Oct. 18, 2015

(86) PCT No.: PCT/CN2015/092148
§ 371 (c)(1),
(2) Date: Oct. 28, 2016

(87) PCT Pub. No.: WO2016/188021
PCT Pub. Date: Dec. 1, 2016

(65) Prior Publication Data
US 2017/0148189 A1  May 25, 2017

(30) Foreign Application Priority Data

May 22, 2015 (CN) .......................... 2015 1 0266796

(51) Int. Cl.
*A61F 9/08* (2006.01)
*G01J 3/46* (2006.01)
(Continued)

(52) U.S. Cl.
CPC .................. *G06T 7/90* (2017.01); *A61F 9/08* (2013.01); *G01J 3/465* (2013.01); *G06K 9/4652* (2013.01);
(Continued)

(58) Field of Classification Search
None
See application file for complete search history.

(56) References Cited

U.S. PATENT DOCUMENTS 6,985,524 B1 * 1/2006 Borchers .............. G09B 21/008
345/549
9,430,954 B1 * 8/2016 Dewhurst ............ G09B 21/007
(Continued)

FOREIGN PATENT DOCUMENTS

| CN | 101458817 A | 6/2009 |
|---|---|---|
| CN | 103177259 A | 6/2013 |

(Continued)

OTHER PUBLICATIONS

Feb. 16, 2016—(WO) International Search Report and Written Opinion Appn PCT/CN2015/092148 with English Tran.
(Continued)

*Primary Examiner* — Kim Y Vu
*Assistant Examiner* — Nathan J Bloom
(74) *Attorney, Agent, or Firm* — Banner & Witcoff, Ltd.

(57) ABSTRACT

A color identifying system, a color identifying method and a display device are provided. The color identifying system comprises an image acquiring unit, a color analyzing unit and an information output unit; the image acquiring unit is configured to acquire an image of an object to be identified; the color analyzing unit is configured to extract profiles of the pattern regions of the object to be identified, and analyze colors of the pattern regions, to determine overall color information of the object to be identified; and the information output unit is configured to output the overall color information of the object to be identified. The color identifying system can help a color vision defective person to identify color of an object, which is greatly convenient to production and life of the color vision defective person, and (Continued)

thus significantly improving quality of life of the color vision defective person.

16 Claims, 2 Drawing Sheets

(51) Int. Cl.
    *G06K 9/46*     (2006.01)
    *G06K 9/62*     (2006.01)
    *G06T 7/11*     (2017.01)
    *G06T 7/90*     (2017.01)

(52) U.S. Cl.
    CPC .............. *G06K 9/6202* (2013.01); *G06T 7/11* (2017.01); *G06T 2207/10024* (2013.01)

(56) References Cited

U.S. PATENT DOCUMENTS

| | | | | |
|---|---|---|---|---|
| 2002/0174085 A1* | 11/2002 | Nelson | ................... | H04L 67/36 |
| 2003/0161529 A1 | 8/2003 | Shimoyama | | |
| 2004/0085327 A1* | 5/2004 | Jones | ................... | G09B 29/003 |
| | | | | 345/591 |
| 2005/0007449 A1* | 1/2005 | Ikado | ................... | G09B 21/008 |
| | | | | 348/62 |
| 2007/0288435 A1* | 12/2007 | Miki | ................... | G06F 17/3025 |
| 2010/0232688 A1 | 9/2010 | Komiya et al. | | |
| 2011/0043644 A1* | 2/2011 | Munger | ............... | G02B 27/017 |
| | | | | 348/207.1 |
| 2014/0355874 A1* | 12/2014 | Sakamaki | ............. | H04N 1/622 |
| | | | | 382/165 |
| 2016/0148354 A1* | 5/2016 | Finlayson | ............... | G06T 5/007 |
| | | | | 382/164 |
| 2017/0200289 A1* | 7/2017 | Gershon | ................... | G06T 7/90 |

FOREIGN PATENT DOCUMENTS

| | | | |
|---|---|---|---|
| CN | 103310201 A | 9/2013 |
| CN | 104200249 A | 12/2014 |
| CN | 104268508 A | 1/2015 |
| CN | 104537354 A | 4/2015 |
| CN | 104821000 A | 8/2015 |
| CN | 204631946 U | 9/2015 |

OTHER PUBLICATIONS

Mar. 3, 2017—(CN) first Office Action Appn 201510266796.X with English Tran.

\* cited by examiner

COLOR IDENTIFYING SYSTEM, COLOR IDENTIFYING METHOD AND DISPLAY DEVICE

The application is a U.S. National Phase Entry of International Application No. PCT/CN2015/092148 filed on Oct. 18, 2015, designating the United States of America and claiming priority to Chinese Patent Application No. 201510266796.X filed on May 22, 2015. The present application claims priority to and the benefit of the above-identified applications and the above-identified applications are incorporated by reference herein in their entirety.

TECHNICAL FIELD

The present disclosure relates to a color identifying system, a color identifying method and a display device.

BACKGROUND

A color vision deficiency is a relatively common inherited disease of eyes, and often manifests in incapability of distinguishing or identifying certain colors. A reason thereof is that there are problems in color vision pyramidal cells of the eyes. In people's life and production, especially in fields such as transportation, medicine, textile, instruments and art and so on, if one is not able to correctly identify colors, it will bring great inconvenience.

Due to a defect in identifying colors, a part of the patients deficient in color vision have great distress at the time of shopping. They cannot identify colors, and accordingly they are not confident in their choice of outfits. Therefore, it is very necessary to create a color identifying system for helping the color vision defective persons, which is conducive to improvement of their quality of life.

SUMMARY

The present disclosure provides a color identifying system, a color identifying method and a display device for the technical problems in the known art. The color identifying system can help a color vision defective person to identify color of an object, which is greatly convenient to production and life of the color vision defective person, and thus significantly improving quality of life of the color vision defective person.

At least one embodiment of the present disclosure provides a color identifying system, comprising an image acquiring unit, a color analyzing unit and an information output unit.

The image acquiring unit is connected with the color analyzing unit and the information output unit, and configured to acquire an image of an object to be identified.

The color analyzing unit is connected with the information output unit, and configured to extract profiles of the pattern regions of the object to be identified in the image, and analyze colors of the pattern regions, to determine overall color information of the object to be identified.

The information output unit is configured to output the overall color information of the object to be identified.

Optionally, the color analyzing unit is configured to divide the object to be identified in the image into a plurality of sub-regions, and analyze and determine colors of the respective sub-regions, then aggregate color information of the respective sub-regions according to pattern regions where the respective sub-regions are located, so as to finally determine the overall color information of the object to be identified.

The information output unit is further configured to output the profiles of the pattern regions of the object to be identified.

Optionally, the color analyzing unit includes an extracting module, a dividing module, an analyzing module, a comparing module, a storage module and an aggregating module.

The extracting module is connected with the dividing module and the information output unit, and configured to extract extract profiles of the pattern regions.

The dividing module is connected with the analyzing module, and configured to divide the object to be identified in the image into a plurality of sub-regions.

The analyzing module is connected with the comparing module, and configured to analyze and determine color parameters of the respective sub-regions.

The storage module is configured to store a sample color database which includes color parameters of all colors.

The comparing module is connected with the storage module, and the comparing module is configured to compare color parameters of the respective sub-region with color parameters in the sample color database, and when a comparison result shows that the parameters are consistent, a color in the sample color database corresponding to the sub-region is determined as color of the sub-region.

The aggregating module is connected with the comparing module, and configured to aggregate colors of the sub-regions correspondingly located in the pattern region, to determine color information of the pattern region, thereby finally determining overall color information of the object to be identified.

Optionally, color parameters of the sub-region include hue, saturation and value parameters.

The sample color database includes hue, saturation, and value parameters of all colors in a hexagonal pyramid color model.

Optionally, the object to be identified has a plurality of pattern regions, the aggregating module includes a grouping sub-module and a statistic sub-module, and the grouping sub-module is connected with the statistic sub-module.

The grouping sub-module is configured to divide the sub-regions correspondingly located in each of the pattern regions into a plurality of first groups, wherein, each of the first groups includes the plurality of sub-regions adjacent to each other; and the grouping sub-module is further configured to divide the first groups correspondingly located in each of the pattern regions into a plurality of second groups, wherein, each of the second groups includes the plurality of first groups adjacent to each other.

The statistic sub-module is configured to perform statistics on color information of the sub-regions in each of the first groups, and determine color information having a statistical result exceeding a threshold as color information of the first group; and further configured to perform statistics on color information of the first groups in each of the second groups, and determine color information having a statistical result exceeding the threshold as color information of the second group.

The statistic sub-module is further configured to perform statistics on color information of the second groups in each of the pattern regions, and determine color information having a statistical result exceeding the threshold as color information of the pattern region.

Optionally, the information output unit is connected with the statistic sub-module, and configured to output color information of the respective pattern regions in a manner of text or voice.

Optionally, a background color of the object to be identified in the image is any color except a first color, and contours of profiles of the pattern regions of the object to be identified adopt the first color, and texts for displaying color information of the pattern regions are located in a background region of the object to be identified and adopt the first color; and the first color is a color which can be identified by a color vision defective person.

The information output unit is configured to display the contours of the profiles.

Optionally, the color identifying system further comprises a color matching unit; the color matching unit is connected with the storage module and the information output unit, and the storage module is further configured to store a color matching scheme; the color matching unit is configured to select, according to color information of the pattern region of the object to be identified, a color matching scheme corresponding thereto from the storage module; and the information output unit is further configured to output the color matching scheme corresponding to the color information of the pattern region of the object to be identified.

Optionally, the color matching scheme includes a plurality of contrast color matching schemes, a plurality of coordinated color matching schemes and a plurality of mainstream color matching schemes.

The sample color database includes a hexagonal pyramid color model, the contrast color matching scheme is configured to match colors in opposite sides of the hexagonal pyramid in the hexagonal pyramid color model or match colors in opposite sides of the hexagonal pyramid and colors on both sides adjacent to the opposite sides in the hexagonal pyramid color model; the coordinated color matching scheme is configured to match colors on 2 to 4 sides of the hexagonal pyramid in the hexagonal pyramid color model, which 2 to 4 sides are connected in sequence and one side therein is adjacent to at least one of the other remaining sides therein; and the mainstream color matching scheme is a popular color matching scheme at present.

Optionally, the information output unit is configured to output the color matching scheme corresponding to color information of the pattern region of the object to be identified in a manner of text plus image or voice plus image.

At least one embodiment of the present disclosure further provides a display device, comprising the color identifying system described above.

At least one embodiment of the present disclosure further provides a color identifying method, comprising:

Acquiring an image of an object to be identified;

Extracting profiles of pattern regions of the object to be identified in the image, and analyzing colors of the pattern regions, to determine overall color information of the object to be identified;

Outputting the overall color information of the object to be identified.

Optionally, the method further comprises:

Outputting the profiles of the pattern regions of the object to be identified;

The analyzing colors of the pattern regions to determine overall color information of the object to be identified includes:

Dividing the object to be identified in the image into a plurality of sub-regions; analyzing and determining colors of the respective sub-regions; then aggregating color information of the respective sub-regions according to pattern regions where the respective sub-regions are located, so as to finally determine the overall color information of the object to be identified.

Optionally, the analyzing and determining color of the respective sub-regions includes, for example:

Analyzing and determining color parameters of the respective sub-regions;

Comparing color parameters of the respective sub-region with color parameters stored in a sample color database; and Determining a color in the sample color database corresponding to the sub-region as color of the sub-region, when a comparison result shows that the parameters are consistent.

Optionally, the aggregating color information of the respective sub-regions according to pattern regions where the respective sub-regions are located, so as to finally determine the overall color information of the object to be identified includes, for example:

The object to be identified having a plurality of pattern regions, dividing the sub-regions correspondingly located in each of the pattern regions into a plurality of first groups, wherein, each of the first groups includes the plurality of sub-regions adjacent to each other;

Dividing the first groups correspondingly located in each of the pattern regions into a plurality of second groups, wherein, each of the second groups includes the plurality of first groups adjacent to each other;

Performing statistics on color information of the sub-regions in each of the first groups, and determining color information having a statistical result exceeding a threshold as color information of the first group;

Performing statistics on color information of the first groups in each of the second groups, and determining color information having a statistical result exceeding the threshold as color information of the second group;

Performing statistics on color information of the second groups in each of the pattern regions, and determining color information having a statistical result exceeding the threshold as color information of the pattern region.

Optionally, the method further comprises:

Selecting, according to color information of the pattern region of the object to be identified, a color matching scheme corresponding thereto from the stored color matching schemes;

Outputting the color matching scheme corresponding to the color information of the pattern region of the object to be identified.

A color identifying system provided by at least one embodiment of the present disclosure can help a color vision defective person to identify color of an object by arranging an image acquiring unit, a color analyzing unit and an information output unit, which is greatly convenient to production and life of the color vision defective person, and thus significantly improving quality of life of the color vision defective person.

A display device provided by at least one embodiment of the present disclosure can help a color vision defective person to identify color of an object by using the color identifying system described above, and thus quality of life of the color vision defective person is significantly improved.

DETAILED DESCRIPTION

In order to make those skilled in the art understand technical solutions of the present disclosure better, a color identifying system, a color identifying method and a display device provided by the present disclosure are further described in detail in conjunction with accompanying drawings and specific implementations hereinafter.

First Embodiment

Figure 1:
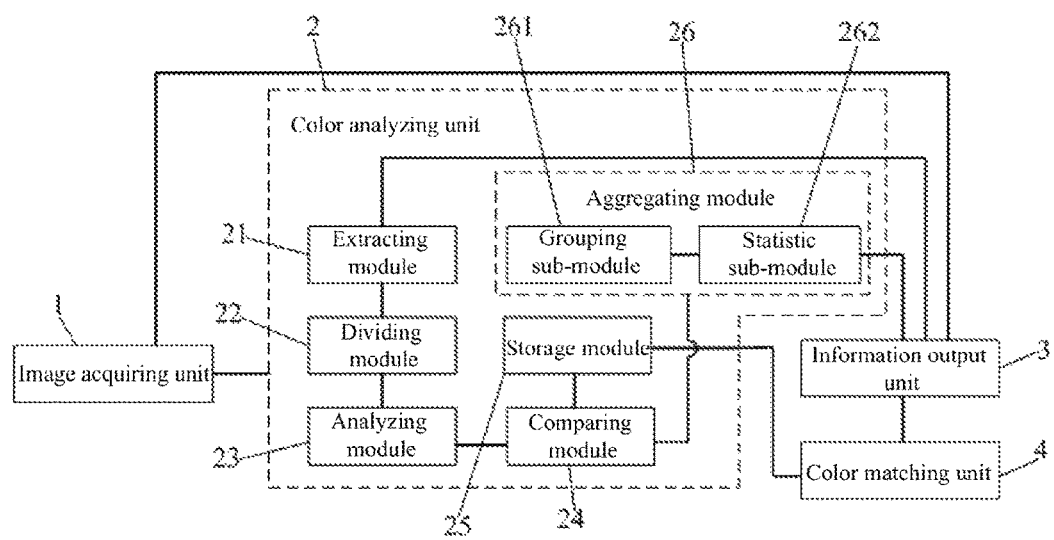
FIG. 1 is a schematic block diagram of a color identifying system in a first embodiment of the present disclosure.

The embodiment provides a color identifying system, which is configured to help a color vision defective person to identify color of an object, and FIG. 1 is a schematic block diagram of a color identifying system in the embodiment. As shown in FIG. 1, the color identifying system comprises an image acquiring unit 1, a color analyzing unit 2 and an information output unit 3. The image acquiring unit 1 is connected with the color analyzing unit 2 and the information output unit 3, and configured to acquire an image of an object to be identified. The color analyzing unit 2 is connected with the information output unit 3, and configured to extract profiles of the pattern regions of the object to be identified in the image, and analyze colors of the pattern regions, to determine overall color information of the object to be identified. The information output unit 3 is configured to output the overall color information of the object to be identified.

The arrangement of the image acquiring unit 1, the color analyzing unit 2 and the information output unit 3 can help a color vision defective person to identify color of an object, which is greatly convenient to production and life of the color vision defective person, and thus significantly improving quality of life of the color vision defective person.

The color analyzing unit 2 is configured to divide the object to be identified in the image into a plurality of sub-regions, analyze and determine colors of the respective sub-regions, then aggregate color information of the respective sub-regions according to pattern regions where the respective sub-regions are located, so as to finally determine the overall color information of the object to be identified. The information output unit 3 is further configured to output the profiles of the pattern regions of the object to be identified. In this way, the color vision defective person may better identify the pattern region in the object to be identified.

In the embodiment, the color analyzing unit 2 includes an extracting module 21, a dividing module 22, an analyzing module 23, a comparing module 24, a storage module 25 and an aggregating module 26. The extracting module 21 is connected with the dividing module 22 and the information output unit 3, and configured to extract profiles of the pattern regions of the object to be identified in the image; and the information output unit 3 is further configured to display contours of the profiles. The dividing module 22 is connected with the analyzing module 23, and configured to divide the object to be identified in the image into a plurality of sub-regions having a same size and shape. The analyzing module 23 is connected with the comparing module 24, and configured to analyze and determine color parameters of the respective sub-regions. The comparing module 24 is connected with the storage module 25, and the storage module 25 is configured to store a sample color database which includes color parameters of all colors. The comparing module 24 is configured to compare color parameters of the respective sub-region with color parameters in the sample color database, and when a comparison result shows that the parameters are consistent, a color in the sample color database corresponding to the sub-region is determined as color of the sub-region. The aggregating module 26 is connected with the comparing module 24, and configured to aggregate colors of the sub-regions correspondingly located in the pattern region, so as to determine color information of the pattern region, thereby finally determining the overall color information of the object to be identified.

It should be noted that, the smaller an area of the sub-region is (i.e., the smaller the sub-region is divided), the more accurately the overall color information of the object to be identified is analyzed. In the embodiment, the area of the sub-region is a total area of four to six pixels.

With the comparing module 24, colors of the respective sub-regions can be accurately determined, thereby well preparing for determining color information of the pattern region. With the aggregating module 26, color information of the pattern region can be accurately determined. And since the image of the object to be identified is divided into one or a plurality of pattern regions, the overall color information of the object to be identified is finally determined after the color information of the pattern region is determined. The overall color information of the object to be identified is color information of all pattern regions in the object to be identified.

Color parameters of the sub-region include hue, saturation, and value parameters. The sample color database includes hue, saturation, and value parameters of all colors in a hexagonal pyramid color model (i.e., HSV color model). Color of each sub-region is determined by comparing color parameters of each sub-region with color parameters of all colors in the hexagonal pyramid color model, which may improve accuracy of the analyzing of color of the sub-region, so that finally determined color of the sub-region is more accurate, thereby improving a color identifying accuracy of the color identifying system.

It should be noted that, there may be limited types of colors stored in the sample color database, for example, color circles of twelve colors are stored, and the twelve colors are white, red, orange, yellow, yellowish-green, green, turquoise, blue, blue-violet, violet, violet-red and black, and however, the hue, saturation and value parameters of those types of colors cover hue, saturation and value parameters of all colors, that is, all colors are finally classified into those types of colors according to hue, saturation and value parameters thereof. In such arrangement, the color identifying system is ensured to identify any color, so that the color identifying system does not have a color identifying blind zone, and further a capability of identifying colors of the color identifying system is more powerful.

In the embodiment, the object to be identified has a plurality of pattern regions, and the aggregating module 26 includes a grouping sub-module 261 and a statistic sub-module 262. The grouping sub-module 261 is connected with the statistic sub-module 262; the grouping sub-module 261 is configured to divide the sub-regions correspondingly located in each pattern region into a plurality of first groups, wherein, each first group includes a plurality of sub-regions adjacent to each other; and further configured to divide the first groups correspondingly located in each pattern region into a plurality of second groups, wherein, each second group includes a plurality of first groups adjacent to each other. The statistic sub-module 262 is configured to perform statistics on color information of the sub-regions in each first group, and determine color information having a statistical result exceeding a threshold as color information of the first group; and further configured to perform statistics on color information of the first groups in each second group, and determine color information having a statistical result exceeding the threshold as color information of the second group; and the statistic sub-module 262 is further configured to perform statistics on color information of the second groups in each pattern region, and determine color information having a statistical result exceeding the threshold as color information of the pattern region.

It should be noted that, the greater a number of the sub-regions in each first group is, the more accurate a result of the analyzing of the color information of each first group is. Similarly, the greater a number of the first groups in each second group is, the more accurate a result of the analyzing of the color information of each second group is. The more accurate the result of the analyzing of the color information of each second group is, the more accurate a result of the analyzing of the color information of each pattern region is. In the embodiment, 5 to 9 sub-regions are divided into a first group, and 3 to 6 first groups are divided into a second group, wherein, the threshold is 70% to 90% of the statistical result, that is, a color accounting for above 70% to 90% in a statistical result of color information of the respective first group is finally determined as color of the first group; and a color accounting for above 70% to 90% in a statistical result of color information of the respective second group is finally determined as color of the second group; and a color accounting for above 70% to 90% in a statistical result of color information of the respective pattern region is finally determined as color of the pattern region.

With the grouping sub-module 261 and the statistic sub-module 262, the result of the analyzing of color information of the respective pattern regions may be more accurate, so that a capability of identifying colors of the color identifying system is more powerful, and the color vision defective person is well helped to identify colors.

In the embodiment, the information output unit 3 is connected with the statistic sub-module 262, and configured to output color information of the respective pattern regions in a manner of text, so as to greatly facilitate the color vision defective person to identify overall color of the object to be identified.

It should be noted that, the information output unit 3 may also output color information of the respective pattern regions in a manner of voice, so as to help the color vision defective person to identify overall color of the object to be identified.

In the embodiment, a background color of the object to be identified in the image is any color except a first color, and contours of profiles of the pattern regions of the object to be identified adopt the first color, and texts for displaying color information of the pattern region are located in a background region of the object to be identified and adopt the first color. The first color is a color which can be identified by a color vision defective person. The information output unit 3 is configured to display the contours of the profiles.

For example, a background color of the object to be identified in the image is any color except black color, and a whole profile of the object to be identified and contours of profiles of the respective pattern regions of the object to be identified adopt black color, and texts for displaying color information of the respective pattern regions are located in a background region of the object to be identified and adopt the black color.

In addition, for example, if a background color of the object to be identified in the image is any color except white color, a whole profile of the object to be identified and contours of profiles of the respective pattern regions of the object to be identified adopt white color, and texts for displaying color information of the respective pattern regions are located in a background region of the object to be identified and adopt the white color.

Because the color vision defective person usually can identify black and white, in a case where the background color is not black, the contours of the pattern regions, the whole contour of the object to be identified and the texts for displaying the color information adopt black; and in a case where the background color is not white, the contours of the pattern regions, the whole contour of the object to be identified and the texts for displaying the color information adopt white. In this way, it is convenient for the color vision defective person to identify colors of the respective pattern regions through the texts and the contours.

It should be noted that, the texts for displaying the color information thereof corresponding to the respective pattern regions point to the respective pattern regions through arrows, wherein, the arrows have a same color as the texts.

In addition, the texts for displaying the color information of the respective pattern regions may be further marked in the respective pattern regions. However, if color of the pattern region is black, color of the text cannot be black, and in this case, the color of the text may be white. If color of the pattern region is white, color of the text cannot be white, and in this case, the color of the text may be black. If color of the pattern region is any other color except black and white, color of the text may be black or white. In this way, it is convenient for the color vision defective person to identify color of the pattern region through the text.

In the embodiment, the color identifying system further comprises a color matching unit 4. The color matching unit 4 is connected with the storage module 25 and the information output unit 3, and the storage module 25 is further configured to store a color matching scheme. The color matching unit 4 is configured to select a color matching scheme corresponding to color information of the at least one pattern region of the object to be identified from the storage module 25 according to the color information of the at least one pattern region of the object to be identified. The information output unit 3 is further configured to output the color matching scheme corresponding to the color information of the at least one pattern region of the object to be identified. That is, the color matching unit 4 not only can select a color matching scheme according to color information of any one pattern region of the object to be identified, but also can select a color matching scheme according to color information of several pattern regions of the object to be identified or overall color information of the object to be identified.

With the color matching unit 4, experience of the color vision defective person on matching colors can be improved, which makes life of the color vision defective person more colorful.

In the embodiment, the color matching scheme includes a plurality of contrast color matching schemes, a plurality of coordinated color matching schemes and a plurality of mainstream color matching schemes. The sample color database includes a hexagonal pyramid color model, and the contrast color matching scheme is configured to match colors in opposite sides of the hexagonal pyramid in the hexagonal pyramid color model or match colors in opposite sides of the hexagonal pyramid and colors on both sides adjacent to the opposite sides in the hexagonal pyramid color model. The coordinated color matching scheme is configured to match colors on 2 to 4 sides of the hexagonal pyramid in the hexagonal pyramid color model, which 2 to 4 sides are connected in sequence and one side therein is adjacent to at least one of the other remaining sides therein. For example, assuming that the six sides connected in sequence in the hexagonal pyramid color model are marked as A, B, C, D, E, and F, and that the coordinated color matching scheme is configured to match colors on 4 sides of the hexagonal pyramid in the hexagonal pyramid color model, then the 4 sides can be A, B, C and D, or can be B, C, D and E, and so on. The mainstream color matching scheme is a popular color matching scheme at present. With multiple types of color matching schemes, experience of the color vision defective person on matching colors can be enriched.

In the embodiment, the information output unit 3 is configured to output the color matching scheme corresponding to color information of the at least one pattern region of the object to be identified in a manner of text plus image. Of course, the information output unit 3 can also output the color matching scheme corresponding to color information of the at least one pattern region of the object to be identified in a manner of voice plus image. Thus, it is convenient for the color vision defective person to identify and experience the color matching scheme.

Figure 2:
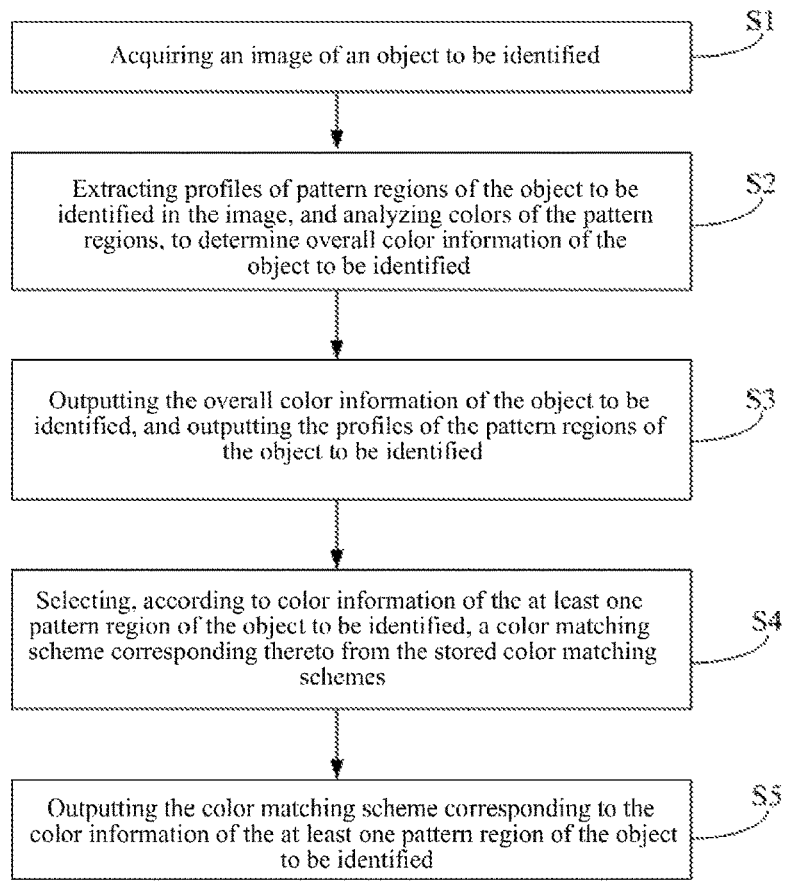
FIG. 2 is a flowchart of a color identifying method in the first embodiment of the present disclosure.
Figure 3:
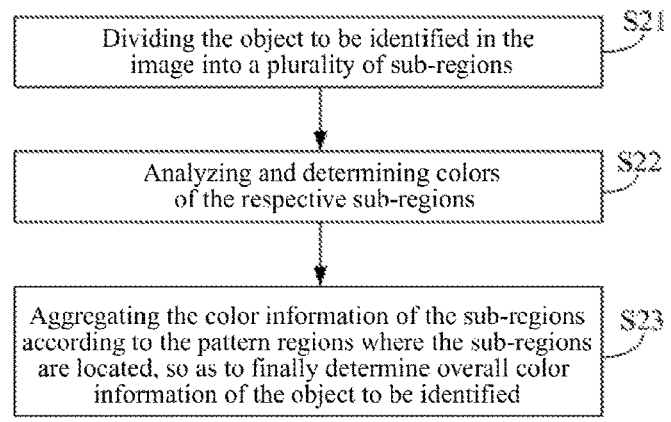
FIG. 3 is a specific flowchart of a second step S2 of FIG. 2.

Based on the color identifying system described above, the embodiment further provides a color identifying method, as shown in FIG. 2 and FIG. 3, which comprises:

Step S1: acquiring an image of an object to be identified.

In the step, a mobile device such as a cell phone or a palmtop computer and so on, in which a color identifying system is built, may be adopted to shoot an image of an object to be identified.

Step S2: extracting profiles of pattern regions of the object to be identified in the image, and analyzing colors of the pattern regions, to determine overall color information of the object to be identified.

In the step, the analyzing colors of the respective pattern regions to determine overall color information of the object to be identified includes:

Step S21: dividing the object to be identified in the image into a plurality of sub-regions.

Step S22: analyzing and determining colors of the respective sub-regions.

The step, for example, includes: analyzing and determining color parameters of the respective sub-regions; comparing color parameters of the respective sub-region with color parameters stored in a sample color database; and when a comparison result shows that the parameters are consistent, determining a color in the sample color database corresponding to the sub-region as color of the sub-region.

Step S23: aggregating color information of the respective sub-regions according to pattern regions where the respective sub-regions are located, so as to finally determine the overall color information of the object to be identified.

The step, for example, includes: the object to be identified having a plurality of pattern regions, dividing the sub-regions correspondingly located in each pattern region into a plurality of first groups, wherein, each first group includes a plurality of sub-regions adjacent to each other; dividing the first groups correspondingly located in each pattern region into a plurality of second groups, wherein, each second group includes a plurality of first groups adjacent to each other; performing statistics on color information of the sub-regions in each first group, and determining color information having a statistical result exceeding a threshold as color information of the first group; and performing statistics on color information of the first groups in each second group, and determining color information having a statistical result exceeding the threshold as color information of the second group; performing statistics on color information of the second groups in each pattern region, and determining color information having a statistical result exceeding the threshold as color information of the pattern region.

Overall color information of the object to be identified is finally determined after the color information of the respective pattern regions is determined.

Step S3: outputting the overall color information of the object to be identified.

The step further includes outputting profiles of the pattern regions of the object to be identified.

The color vision defective person is helped to identify colors of objects through steps S1 to S3 described above, which is greatly convenient to production and life of the color vision defective person.

In the embodiment, the color identifying method further comprises step S4: selecting, according to color information of the at least one pattern region of the object to be identified, a color matching scheme corresponding thereto from the stored color matching schemes.

Step S5: outputting the color matching scheme corresponding to the color information of the at least one pattern region of the object to be identified.

Experience of the color vision defective person on matching colors can be improved through steps S4 to S5 described above, which makes life of the color vision defective person more colorful.

Advantageous effects of the first embodiment: the color identifying system provided by the first embodiment can help a color vision defective person to identify color of an object with the arrangement of an image acquiring unit, a color analyzing unit and an information output unit, which is greatly convenient to production and life of the color vision defective person, and thus significantly improving quality of life of the color vision defective person.

Second Embodiment

The embodiment provides a display device, comprising the color identifying system in the first embodiment.

By using the color identifying system in the first embodiment, the display device can help a color vision defective person to identify and match color of an object, which greatly improves quality of life of the color vision defective person.

It should be understood that the foregoing embodiments are only exemplary embodiments of the present disclosure to describe the principle of the present disclosure; however, the present disclosure is not limited thereto. Those ordinarily skilled in the art can make various variations and improvements without departing from the spirit and essence of the present disclosure, and such variations and improvements also fall into the protection scope of the present disclosure.

The application claims priority of Chinese Patent Application No. 201510266796.X filed on May 22, 2015, the disclosure of which is incorporated herein by reference in its entirety as part of the present application.

The invention claimed is:

1. A color identifying system, comprising a processor configured to perform steps of:
acquiring an image comprising an object to be identified;
extracting profiles of pattern regions of the object to be identified in the image, and analyze colors of the pattern regions, to determine overall color information of the object to be identified; and
displaying text indicating the colors of the pattern regions on the image or producing voice indicating the colors of the pattern regions, based on the overall color information;
wherein, the object to be identified has a plurality of pattern regions, and the processor is further configured to perform steps of:
dividing sub-regions correspondingly located in each of the pattern regions into a plurality of first groups, wherein each of the first groups includes a plurality of the sub-regions adjacent to each other, and further dividing the first groups correspondingly located in each of the pattern regions into a plurality of second groups, wherein each of the second groups includes a plurality of the first groups adjacent to each other;
performing statistics on color information of the sub-regions in each of the first groups, and determining color information having a statistical result exceeding a threshold as color information of the first group, and further performing statistics on color information of the first groups in each of the second groups, and determining color information having a statistical result exceeding the threshold as color information of the second group; and
performing statistics on color information of the second groups in each of the pattern regions, and determining color information having a statistical result exceeding the threshold as color information of the pattern region.

2. The color identifying system according to claim 1, wherein the processor is further configured to perform steps of: dividing the object to be identified in the image into a plurality of sub-regions, and analyzing and determining colors of respective sub-regions, then aggregating color information of the respective sub-regions according to pattern regions where the respective sub-regions are located, so as to finally determine the overall color information of the object to be identified; and
outputting the profiles of the pattern regions of the object to be identified.

3. The color identifying system according to claim 2, wherein the processor is further configured to perform steps of:
extracting profiles of the pattern regions;
dividing the object to be identified in the image into a plurality of sub-regions;
analyzing and determining color parameters of the respective sub-regions;
storing a sample color database which includes color parameters of all colors;
comparing color parameters of the respective sub-region with color parameters in the sample color database, and when a comparison result shows that the parameters are consistent, a color in the sample color database corresponding to the sub-region is determined as a color of the sub-region; and
aggregating colors of the sub-regions correspondingly located in the pattern region, to determine color information of the pattern region, thereby finally determining the overall color information of the object to be identified.

4. The color identifying system according to claim 3, wherein color parameters of the sub-region include hue, saturation and value parameters; and wherein
the sample color database includes hue, saturation, and value parameters of all colors in a hexagonal pyramid color model.

5. The color identifying system according to claim 3, wherein, a background color of the object to be identified in the image is any color except a first color, and contours of profiles of the pattern regions of the object to be identified adopt the first color, and text for displaying color information of the pattern regions is located in a background region of the object to be identified and adopt the first color; and the first color is a color which can be identified by a color vision defective person; and
the processor is further configured to perform steps of displaying the contours of the profiles.

6. The color identifying system according to claim 3, wherein the processor is further configured to perform steps of: storing a color matching scheme; selecting, according to color information of the pattern region of the object to be identified, a stored color matching scheme corresponding thereto; and outputting the color matching scheme corresponding to the color information of the pattern region of the object to be identified.

7. The color identifying system according to claim 6, wherein the color matching scheme includes a plurality of contrast color matching schemes, a plurality of coordinated color matching schemes, and a plurality of mainstream color matching schemes;
the sample color database includes a hexagonal pyramid color model, the contrast color matching scheme is configured to match colors in opposite sides of the hexagonal pyramid in the hexagonal pyramid color model or match colors in opposite sides of the hexagonal pyramid and colors on both sides adjacent to the opposite sides in the hexagonal pyramid color model; the coordinated color matching scheme is configured to match colors on 2 to 4 sides of the hexagonal pyramid in the hexagonal pyramid color model, which 2 to 4 sides are connected in sequence and one side therein is adjacent to at least one of the other remaining sides therein; and the mainstream color matching scheme is a popular color matching scheme.

8. The color identifying system according to claim 6, wherein the processor is further configured to perform steps of outputting the color matching scheme corresponding to color information of the pattern region of the object to be identified in a manner of text plus image or voice plus image.

9. A display device, comprising the color identifying system according to claim 1.

10. A color identifying method, comprising:
acquiring an image comprising an object to be identified;
extracting profiles of pattern regions of the object to be identified in the image, and analyzing colors of the pattern regions, to determine overall color information of the object to be identified; and
displaying text indicating the colors of the pattern regions on the image or producing voice indicating the colors of the pattern regions, based on the overall color information,
wherein the object to be identified has a plurality of pattern regions, the method further comprising:

dividing sub-regions correspondingly located in each of the pattern regions into a plurality of first groups, wherein, each of the first groups includes a plurality of the sub-regions adjacent to each other;

dividing the first groups correspondingly located in each of the pattern regions into a plurality of second groups, wherein, each of the second groups includes a plurality of the first groups adjacent to each other;

performing statistics on color information of the sub-regions in each of the first groups, and determining color information having a statistical result exceeding a threshold as color information of the first group;

performing statistics on color information of the first groups in each of the second groups, and determining color information having a statistical result exceeding the threshold as color information of the second group; and performing statistics on color information of the second groups in each of the pattern regions, and determining color information having a statistical result exceeding the threshold as color information of the pattern region.

11. The color identifying method according to claim 10, further comprising:

outputting the profiles of the pattern regions of the object to be identified, wherein the analyzing colors of the pattern regions, to determine overall color information of the object to be identified includes:

dividing the object to be identified in the image into a plurality of sub-regions; analyzing and determining colors of respective sub-regions; and then aggregating color information of the respective sub-regions according to pattern regions where the respective sub-regions are located, so as to finally determine the overall color information of the object to be identified.

12. The color identifying method according to claim 11, wherein, the analyzing and determining colors of the respective sub-regions includes:

analyzing and determining color parameters of the respective sub-regions;

comparing color parameters of the respective sub-region with color parameters stored in a sample color database; and determining a color in the sample color database corresponding to the sub-region as a color of the sub-region, when a comparison result shows that the parameters are consistent.

13. The color identifying method according to claim 10, further comprising:

selecting, to color information of the pattern region of the object to be identified, a color matching scheme corresponding thereto from stored color matching schemes; and outputting the color matching scheme corresponding to the color information of the pattern region of the object to be identified.

14. The color identifying system according to claim 4, wherein the object to be identified has a plurality of pattern regions, and the processor is further configured to perform steps of:

dividing the sub-regions correspondingly located in each of the pattern regions into a plurality of first groups, wherein each of the first groups includes a plurality of the sub-regions adjacent to each other, and further dividing the first groups correspondingly located in each of the pattern regions into a plurality of second groups, wherein each of the second groups includes a plurality of the first groups adjacent to each other;

performing statistics on color information of the sub-regions in each of the first groups, and determining color information having a statistical result exceeding a threshold as color information of the first group; and further performing statistics cm color information of the first groups in each of the second groups, and determining color information having a statistical result exceeding the threshold as color information of the second group; and performing statistics on color information of the second groups in each of the pattern regions, and determining color information having a statistical result exceeding the threshold as color information of the pattern region.

15. The color identifying system according to claim 4, wherein a background color of the object to be identified in the image is any color except a first color, and contours of profiles of the pattern regions of the object to be identified adopt the first color, and text fix displaying color information of the pattern regions is located in a background region of the object to be identified and adopt the first color; and the first color is a color which can be identified by a color vision defective person; and the processor is further configured to perform steps of displaying the contours of the profiles.

16. The color identifying system according to claim 1, wherein a background color of the object to be identified in the image is any color except a first color, and contours of profiles of the pattern regions of the object to be identified adopt the first color, and text for displaying color information of the pattern regions is located in a background region of the object to be identified and adopt the first color; and the first color is a color which can be identified by a color vision defective person; and the processor is further configured to perform steps of displaying the contours of the profiles.

* * * * *